United States Patent [19]

Yamamoto et al.

[11] 3,954,663
[45] May 4, 1976

[54] PROCESS FOR THE PREPARATION OF LIMULINA LYSATE

[75] Inventors: Masaaki Yamamoto, Yokohama; Masayoshi Kobayashi, Kawasaki; Sashichi Okabe, Tokyo, all of Japan

[73] Assignee: Teikoku Horinine Mfg. Co. Ltd., Tokyo, Japan

[22] Filed: Dec. 10, 1973

[21] Appl. No.: 423,552

[30] Foreign Application Priority Data
Dec. 18, 1972  Japan............................ 47-126161
Nov. 19, 1973  Japan............................ 48-129147

[52] U.S. Cl............................. 252/408; 23/230 B; 195/99; 195/103.5 R; 424/2; 424/12; 424/95; 424/101; 424/253
[51] Int. Cl.$^2$.................... C09K 3/00; G01N 31/00; G01N 33/16; C12K 1/04; A61K 35/56; A61K 31/52
[58] Field of Search.............. 252/408; 424/101, 95, 424/253, 12, 2; 23/230 B; 195/99, 103.5 R

[56] References Cited
UNITED STATES PATENTS
3,729,947   5/1973   Higuchi............................... 424/101
3,740,433   6/1973   Clody et al. ........................ 424/253

OTHER PUBLICATIONS
Thye Yin, E., et al.; Biochem. Biophys. Acta., Vol. 261, p. 284–289 (Jan. 1972).
Bryan, F. T.; et al.; Science, Vol. 144, p 1147–1148 (May 1964).
Chemical Abstracts, Vol. 78, 95202q (Jan.–June 1973).
Chemical Abstracts, Vol. 76, 70459z (Jan.–June 1972).
Chemical Abstracts, Vol. 69, 9114x (1968).
Chemical Abstracts, Vol. 79, 28578z (June–Dec. 1973).
Hochstein, Donald H., et al., Bulletin of the Parenteral Drug Association, Vol. 27, No. 3, pp. 139–148 (6/73).
Solum, N. O.; Thrombosis Et Diathesis Haemorrhagica, Vol. 23, pp. 170–181 (1970).

*Primary Examiner*—Benjamin R. Padgett
*Assistant Examiner*—T. S. Cron
*Attorney, Agent, or Firm*—Sherman & Shalloway

[57] ABSTRACT

A process comprising extracting the blood of horseshoe crabs (Limulina) into an isotonic buffer solution containing an agent which inhibits the agglutination of amebocyte, separating the amebocyte from said solution, breaking the amebocyte, and recovering Limulina lysate, which is characterized in that methyl derivatives of xanthine such as theophyline, theobromine, or caffeine, or their salts, are used as the amebocyte's agglutination-inhibiting agent is disclosed.

19 Claims, No Drawings
}

PROCESS FOR THE PREPARATION OF LIMULINA LYSATE

This invention relates to a process for the preparation of lysate or pregel which is useful for the detection and/or determination of endotoxin including pyrogens. More particularly, the invention relates to a process for recovering Limulina lysate from the blood of horseshoe crabs (Limulina) at an extremely high yield.

Conventionally, the detection of trace amounts of endotoxin present in the blood of men infected with germs, or that of pyrogen containing medicines, has been performed by utilization of biological response. However, in an vivo test for that purpose meets many difficulties, in that it requires a large number of experimental animals for detecting only one sample to be tested and that it must be performed through complex and delicate procedures. For example, the detection of pyrogen utilizing biological response is normally performed by injecting the test liquid into experimental animals, mainly rabbits, and observing the temperature rise of the animals. Or, in certain cases an epinephrine sensitivity test or the like is utilized. However, because those methods depend upon biological response, error due to individual differences among the test animals is great. Such low precision of the test, together with the complicated test procedures, makes the quantitative determination of pyrogen in the test sample virtually impossible. Furthermore, the conventional methods require large numbers of experimental animals which call for enormous expense and labor for their feeding and management.

Recently, F. B. Bang discovered that the lysate (amebocyte extract) from the amebocyte separated from the blood of American horseshoe crabs (*Limulus polyphemus*) incites a unique gellation reaction with the endotoxin of gram-negative bacteria [*Bull. Johns Hopkins Hosp.*, 98 325 (1956)], which gave rise to the search for a simple and precise detection or determination of endotoxin of gram-negative bacteria.

As soon as the blood of horseshoe crab is extracted from the body, the amebocyte becomes adhesive and agglutinates, and is broken to discharge its content. Therefore, for the safe separation of amebocyte extracted from the blood of horseshoe crabs, it is necessary to add an amebocyte-agglutination-inhibiting agent to the extracted blood upon extraction to prevent the amebocyte from coagulation and agglutination. The amebocyte of horseshoe crabs however is entirely different from erythrocyte of warm blooded animals, and citric acid, heparin, etc. which are frequently used as the anticoagulant for the blood of warm blooded animals are entirely ineffective for amebocyte preservation. N-ethylmaleimide has been proposed as an effective anti-amebocyte agglutination agent for horseshoe crab's blood [Science, 144, 1147 – 8 (1964)].

However, N-ethylmaleimide exhibits insufficient anti-amebocyte agglutination action, and cannot prevent considerable amebocyte agglutination from occurring during blood extraction, amebocyte separation, and/or washing of amebocyte, depending on the individual differences among the horseshoe crabs. Such agglutination makes the lysate preparation impossible, and thus the ratio of successful lysate preparation normally reaches at best around 30% for the total horseshoe crabs employed. Furthermore, N-ethylmaleimide is extremely volatile, and even an aqueous solution thereof generates toxic gas which is irritant to the operators' eyes and mucous membrane. Thus it is objectionable from the views of hygiene and safety. N-ethylmaleimide also is a very expensive chemical, and unsuitable for commercialization.

We have conducted extensive studies in the search for a method which facilitates the medically and pharmaceutically important diagnosis or detection and determination of pyrogen through simple procedures, and which is free from the foregoing deficiencies of the conventional extraction methods. As a result, we have discovered that the use of methyl derivatives of xanthine or their salts as the agglutination-inhibing agent for the amebocyte makes it possible to perfectly prevent the amebocyte's agglutination during blood extraction, amebocyte separation and/or washing, and allows the recovery of object Limulina lysate in high yield. Furthermore, we also found that the concurrent presence of alkaline earth metal ion in the Limulina lysate at certain concentrations substantially improves the sensitivity for endotoxin of the lysate.

Accordingly, an object of the present invention is to provide a process for recovering Limulina lysate (pregel), which is useful for detecting and/or determining even trace amounts of pyrogen or endotoxin within a short time through simple means, from the blood of horseshoe crabs (Limulina) in high yield.

A further object of the invention is to provide a process for the preparation of Limulina lysate of excellent sensitivity to endotoxin from the blood of horseshoe crabs, (Limulina) in high yield.

Still many other objects and advantages of the present invention will become apparent from the following descriptions.

According to the invention, the foregoing objects are accomplished by the process comprising: extracting the blood of horseshoe crabs (Limulina) into an isotonic buffer solution containing an agent which inhibits the agglutination of amebocyte; separating the amebocyte from said solution; breaking the amebocyte; and recovering Limulina lysate, which process is characterized in that methyl derivatives of xanthine or their salts of the formula,

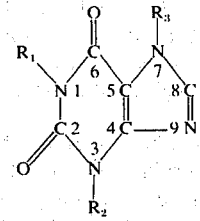

(1)

in which $R_1$, $R_2$ and $R_3$ each represents hydrogen atom or a methyl group, at least one of the $R_1$, $R_2$, and $R_3$ being a methyl group, are used as the amebocyte's agglutination-inhibiting agent.

The use of specified methyl derivatives of xanthine or their salts as the agent for inhibiting agglutination of amebocyte, according to the present invention, substantially eliminates the agglutination of amebocyte during the blood extraction, amebocyte separation, and/or washing procedures. Consequently, the object Limulina lysate can be recovered in high yield quite satisfactorily for industrial practice.

Of the useful methyl derivatives of xanthine of formula (I), particularly
theophylline (1,3-dimethylxanthine),
theobromine (3,7-dimethylxanthine), and
caffeine (1,3,7-trimethylxanthine)
are preferred. Those methyl derivatives of xanthine can be used also in their salt form. As suitable salts, acid addition salts thereof with inorganic or organic acid such as hydrochloric and acetic acids, and alkali salts such as sodium and potassium salts can be named. Particularly the methyl derivatives having low solubility in water, such as theobromine, are used in the salt form with advantage.

As to the horseshoe crabs which donate blood for the subject process, any specific type of crabs belonging to the genus of Limulina can be used. For example, the blood extracted from
*Limulus polyphemus* (Linné),
*Tachypleus tridentatus* (Leach),
*Tachypleus gigas* (Mueller),
*Tachypleus hoeveni* (Pocock), and
*Carcinoscorpius rotundicanda* (LaTreille),
can be used.

Hereinafter the subject process will be explained by the order of the operations.

First the blood of horseshoe crab is extracted into an isotonic buffer solution containing the compound of formula (I). The blood extraction may be performed by any of the means known per se. For instance, the heart puncturatio method is advantageously employed. The cardiac puncturatio method can be practiced either by direct blood extraction wherein the injection needle of suitable inner diameter is connected with a silicon tube, and directly inserted into the heart of the crab from the junction of the thoracic and abdominal position so that the blood is led out into the isotonic buffer solution containing the anti-agglutination agent through the tube, assisted by the inside pressure of the heart (cardiac chamber), or by the indirect blood extraction wherein the injection syringe, which is partly filled with a predetermined quantity of the isotonic buffer solution containing the anti-agglutination agent, is inserted into the heart, and blood is sucked into the syringe as the piston is pulled back. The blood of horseshoe crab can be extracted into the isotonic solution containing the compound of formula (I) by either of the above means. The so-obtained mixture of the isotonic buffer solution and horseshoe crab's blood is extremely stable, without showing amebocyte agglutination after long periods of standing.

The isotonic buffer solution suitably has a pH ranging from 6.0 to 8.0, preferably that of 7.2. Because horseshoe crab's blood is approximately isotonic with sea water, the solution is preferably prepared from artificial sea water or 2.8 – 3.2 wt. % sodium chloride solution as the base. Such an isotonic buffer solution can be prepared, for example, by adding a phosphoric acid buffer solution of pH 6.0 – 8.0 to artificial sea water or to an aqueous sodium chloride solution of 2.8 – 3.2 % by weight in concentration, to form a 0.01M isotonic buffer solution, or by adding sodium chloride to a 0.01M phosphoric acid buffer solution to a concentration of 2.8 – 3.2% by weight and dissolving it, or by replacing the phosphoric acid buffer solution used in the above procedures with tris buffer solution.

The compound of formula (I) should be dissolved in the isotonic buffer solution in advance. The quantitative ratio of the compound of formula (I) may be such that its concentration in the mixture of the isotonic buffer solution and blood obtained upon blood extraction as already described should become 0.5 – 2 mM, preferably 1 mM. In order to make the concentration of the compound of formula (I) in the isotonic buffer solution-blood mixture, for example, 1 mM, therefore, the compound of formula (I) should be dissolved in the isotonic buffer solution prepared as above to a concentration of 2 mM in advance, and after adjusting the pH of the solution to 6.0 – 8.0, preferably 7.2, an equivalent amount thereto of the blood may be sucked thereinto and mixed.

From the so-formed isotonic buffer solution-blood mixture obtained by extracting the blood of horseshoe crab, the amebocyte is isolated by a suitable means. For example, by placing the isotonic buffer solution-blood mixture in a centrifugal precipitation tube, and effecting the centrifugal separation normally at 1,000 – 3,000 rpm for 2 to 10 minutes, the mixture can be advantageously separated into the supernatant composed of the isotonic buffer solution and blood serum, and the lower layer of amebocyte. Thus the amebocyte can be separated from the upper layer by decantation or other means known per se.

The thus-separated amebocyte portion is then washed a few times with the isotonic buffer solution containing the compound of formula (I) as above, and subsequently with the isotonic buffer solution containing none of the compound of formula (I) again a few times.

It is desirable to quickly effect the washing, in order to prevent the amebocyte from agglutination and rupture.

The thus-isolated amebocyte is then left in pyrogen-free water. Whereupon the membrane of the amebocyte is ruptured due to the different osmotic pressure outside and inside of the amebocyte, and the content of amebocyte is extracted into the pyrogen-free water.

The "pyrogen-free water" mentioned herein means the water containing no endotoxin, which can be prepared, for example, by re-distilling distilled water or de-ionized water, and if necessary further sterilizing the same in an autoclave at 120°C. for 30 minutes.

In the above extraction procedure, the rupture of the amebocyte membrane and extraction of amebocyte content can be preferably accelerated by mechanical agitation or freeze thawing of the pyrogen-free water containing the amebocyte, or by subjecting the system to ultrasonic vibration.

The pyrogen-free water is added to the amebocyte at a quantitative ratio of 20 to 50 ml, preferably 30 to 40 ml, per the amount of amebocyte obtained from 100 ml of the blood extracted from horseshoe crab.

We have further discovered that if the pyrogen-free water in the above extraction procedure is replaced by an extraction solvent of pH 6.0 – 8.0 which contains at least one alkaline earth metal ion at a concentration of 2 – 60 mM, Limulina lysate of improved endotoxin sensitivity can be obtained.

As the alkaline earth metal ion, calcium ion and magnesium ion are preferred. Particularly magnesium ion exhibits excellent sensitivity-rising effect and therefore, is the most preferred. The alkali earth metal ions are supplied by dissolving a water-soluble alkaline earth metal salt in water. As such water-soluble alkaline earth metal salt, those inorganic salts such as calcium chloride, magnesium sulfate, etc., can be advantageously used. Particularly the salt having the decomposition point of 170°C. or above is preferred, because the salt must first undergo the pyrogen-elimination treatment. The salt may be used singly or in a combination of plural types.

The alkaline earth metal salt is used in a quantity which will make the alkaline earth metal ion concentration in the aqueous solution 2 to 60 mM. The optimum quantity is variable depending on the kind of ion, individuality of the blood-donating horseshoe crab, and the like, but normally the preferred range for the calcium ion is 2 to 10 mM, inter alia, 4 mM, and 5 to 50 mM for magnesium ion, particularly 20 mM.

It is furthermore discovered according to the present invention that when the said extraction solvent contains alkali metal ion in addition to the alkaline earth metal ion, Limulina lysate of still more-improved endotoxin sensitivity can be obtained.

As the useful alkali metal ion, sodium ion and potassium ion, particularly sodium ion, are the most preferred. The alkali metal ion may be present at a concentration ranging from 10 to 150 mM. The optimum concentration differs depending on the kind of alkali metal and individuality of the blood-donating horseshoe crab. For example, it is from 10 to 150 mM, for sodium ion.

As the source of alkali metal ion supply, water-soluble inorganic alkali metal salts, such as sodium chloride, potassium chloride, etc., can be advantageously used.

The extraction solvent containing the alkali earth metal salt and, if necessary, the alkali metal salt as the solute as above-described should have a pH approximately within the neutral range, i.e., normally the pH of 6.0 to 8.0, particularly from 6.5 to 7.5. Accordingly, when the pH of the pyrogen-free water in which the alkaline earth metal salt and if necessary alkali metal salt are dissolved becomes outside the above-specified range, it should be suitably adjusted with an appropriate acid or alkali.

The extraction may be effected at room temperature, but if necessary slightly reduced temperature such as from 0°C. to 5°C. may be employed.

Thus the lysate is extracted from the amebocyte into the aqueous phase, and upon separating and removing the amebocyte membrane pieces by known separation means such as centrifuge, the object Limulina lysate or pregel can be obtained.

The lysate can be utilized for the detection and/or determination of endotoxin as is, or, may be freeze-dried and powderized improve storage stability.

While it is a preferred practice to introduce the alkaline earth metal ion and optionally alkali metal ion into th lysate by causing their advance presence in the extraction solvent as above-described, we have furthermore discovered in the course of our studies that the alkaline earth metal salt and optionally the alkali metal salt may be added and dissolved in the lysate obtained through the extraction with pyrogen-free water in the described manner, to a concentration within the above-specified range, to provide the Limulina lysate exhibiting equally increased sensitivity to endotoxin.

The freeze-dried powder of the lysate prepared as above is returned to the original lysate form with pyrogen-free water immediately before its usage. It is also possible to introduce the alkaline earth metal ion and optionally alkali metal ion into the lysate reproduced as it was, to increase the latter's sensitivity to endotoxin and is also possible to assay these endotoxins.

It should be understood that those modifications are also covered by the scope of the subject invention.

Incidentally, it should be obvious that in practicing the subject process, all the chemicals and instruments which come in contact with the blood or the amebocyte, such as the tools and containers, reagent, solvent, etc., should be sterilized and subjected to pyrogen-removing treatment in advance, so as to prevent bacterial contamination through out the whole procedure.

The above-described process of the present invention has a number of various advantages as described below.

1. According to the subject process using the methyl derivatives of xanthine or their salts of formula (I) as the amebocyte's agglutination-inhibiting agent, the amebocyte's agglutination in the blood of horseshoe crab is almost perfectly prevented during the blood extraction and amebocyte's separation and washing procedures, regardless of the individual differences among the blood-donating horseshoe crabs. Consequently, the recovery ratio of Limulina lysate or pregal to the blood-donating horseshoe crabs can be remarkably improved.

This advantage can be clearly demonstrated by a comparative experiment described below.

Two types of the lysate were prepared from the blood of each of 30 horseshoe crabs in the manner described in the later-appearing Example 1, using theophylline and N-ethylmaleimide [which is a known amoebocyte agglutination-inhibiting agent] respectively. The activities of the lysates were compared as below.

First the endotoxin extracted from *Salmonella enteritidis*, which is used as a standard endotoxin, was dissolved in a 0.01M phosphate buffer solution having a pH of 6.2, to a concentration of 0.01 µg/ml, and 0.1 ml each of the test solution was added to a small test tube containing 0.1 ml of one of the lysates. After thorough stirring, each test tube was allowed to stand in an incubator maintained at 37°C., to cause gelation. After 60 minutes' standing, the test tubes were withdrawn and inclined by 45° and examined for their state of gelation. The results were shown in the following table, in which the numerals indicate the number of horseshoe crabs, and the marks have the below-specified significations.

Table 1

| Amebocyte's agglutination-inhibiting agent | Lysate's activity | | | | Recovery ratio of lysate exhibiting activities of + and ++ gradings |
|---|---|---|---|---|---|
| | − | ± | + | ++ | |
| Theophylline (this invention) | 0 | 4 | 10 | 16 | 26/30 (86.7%) |
| N-ethylmaleimide (control) | 9 | 11 | 6 | 4 | 10/30 (33.3%) |

++ : a hard gel was formed, which remained static upon the inclination.
+ : a hard gel was formed, which moved as a clot when inclined.
± : a soft, semi-fluidable gel was formed, which flowed when inclined.
− : the system retained the fluid form, showing substantially no change.

As is apparent from the above results, according to the invention the lysate exhibiting excellent endotoxin detectability or sensitivity could be recovered for as much as 86.7% of the horseshoe crabs employed. Thus the waste of the horseshoe crabs which are precious as one of the few ancient creatures still surviving is extremely reduced as compared with the conventional process.

2. The methyl derivatives of xanthine useful for the subject process are invariably non-volatile and non-toxic upon contact. Thus according to the present process the lysate can be prepared through the procedures which are safe and not detrimental to the human body in any manner at all stages. Furthermore, the derivatives as well as their salts are cheap, and the lysate can be prepared at an expense approximately one-hundredth of that of the conventional process employing N-ethylmaleimide. Thus the subject process is economical and industrially feasible.

3. Again according to the present process by using an alkaline earth metal ion-containing extraction solvent, a lysate having excellent endotoxin sensitivity can be obtained which exhibits substantially incrased sensitivity over that of the lysate prepared by the conventional process [Biochem. Biophys. Acta. 261 284 (1972)], not to speak of that prepared by the amebocyte extraction with pyrogen-free water alone.

The above statement can be substantiated by a comparative experiment described below.

To wit the activity of the lysate to 0.1 ml each of the lysate obtained by breaking amebocyte in the solution specified in Table 2 for each run in the previously described manner, 0.1 ml of the test liquid containing the endotoxin from Salmonella enteritidis was added, and the mixture was left standing for an hour at 37°C., and for further 5 minutes at room temperature. Thereafter the activity of the lysate was graded. When the grading was ++, the test body was further diluted and subjected to the same test, until the grading became +. Thus it was confirmed that the presence of alkaline earth metal ion in the extraction solvent conspicuously increases the lysate's sensitivity to endotoxin. The results of the experiment are also shown in Table 2.

tion of gram-negative bacteria and endotoxin thereof which are the cause of sepsis and infection shock, and also the detection and determination of endotoxin in various test liquids such as blood-plasma for transfusion, glucose solution, Ringer's solution, and other venous injection liquids, can be performed with simplicity and ease.

The endotoxin detection can be effected by adding the lysate of this invention to the test sample and observing the occurrence of gelation. Also the determination of endotoxin can be effected by utilizing the close correlation of the intensity of the galation reaction of the test sample occurring upon the addition of a fixed amount of the lysate of this invention, with the quantity of endotoxin. Thus, for example, when the reaction result was ++ in the test described in item (1) above, by consecutively doubling the degree of dilution and repating the above detection reaction until the grading of + is obtained, the minimum endotoxin quantity detectable with the lysate can be determined from the degree of dilution. Also the determination of endotoxin contained in an unknown sample can be easily effected by first reacting the test liquid with the Limulina lysate of the invention to determine the maximum degree of dilution at which the reaction result of + is obtained, and multiplying said degree of dilution by the minimum quantity of the lysate which could detect the endotoxin.

Hereinafter the process of the invention will be explained in further detail, with reference to the working Examples.

EXAMPLE 1

Horseshoe crabs (Tachypleus tridentatus) were disinfected at the back and thoracic and abdominal junction position with 70% ethanol. An injection needle of 13

Table 2

| Run No. | Composition of Amebocyte Extraction Solvent | | | | | Endotoxin[a] Detection Sensitivity | Sensitivity[b] Index |
|---|---|---|---|---|---|---|---|
| | $CaCl_2$ (mM) | $MgSO_4$ (mM) | NaCl (mM) | $H_2O$ (ml) | pH | | |
| 1 | — | — | — | 1000 | 6.8 | $1 \times 10^{-3}$ | 1 |
| 2 | 1 | — | — | 1000 | '' | $5 \times 10^{-4}$ | 2 |
| 3 | .1 | — | 154 | 1000 | '' | $2.5 \times 10^{-4}$ | 4 |
| 4 | 4 | — | — | 1000 | '' | $1 \times 10^{-4}$ | 10 |
| 5 | — | 20 | — | 1000 | '' | $5 \times 10^{-5}$ | 20 |
| 6 | 4 | 20 | — | 1000 | '' | $5 \times 10^{-6}$ | 200 |
| 7 | 4 | 20 | 40 | 1000 | '' | $1 \times 10^{-6}$ | 1000 |
| 8 | 4 | — | 40 | 1000 | '' | $0.625 \times 10^{-4}$ | 16 |
| 9 | — | 20 | 40 | 1000 | '' | $2.5 \times 10^{-5}$ | 40 |

[a] The endotoxin content of the test liquid which gave the + grading when subjected to the endotoxin (Salmonella enteritidis) detection test with the lysate obtained upon breaking the amebocyte in an aqueous solution containing the ion or ions specified for each run.
[b] The sensitivity index of the lysate obtained by breaking the amebocyte with the aqueous solution containing the ion or ions specified for each run, based on that of the lysate obtained by breaking the amebocyte with water which is labelled 1.

As is apparent from the above Table, the lysate of the invention of which the sensitivity is increased with alkaline earth metal ion and optionally alkali metal ion exhibits the endotoxin-detecting ability more than ten times greater than that of the lysate of normal sensitivity, and again at least 2.5 times greater than that of the lysate prepared by the conventional method (Run No. 3). Thus the lysate of the invention possesses very high quality.

The Limulina lysate prepared in accordance with the subject process is useful for the detection and determination of endotoxin.

It is medically and pharmaceutically particularly important to detect and determine endotoxin. With the lysate of this invention, the detection and determinagauge in inner diameter was connected with a silicon tube of approximately 20 cm in length, and the needle was directly inserted into the heart of the crab. An isotonic buffer solution was prepared by dissolving sodium chloride in 0.01M tris buffer solution having a pH of 7.2 to a concentration of 2.95 wt %, and into which theophylline was dissolved to a concentration of 2 mM. The pH of the solution was readjusted to 7.2 with trisaminomethane, and 50 ml each of the so prepared anti-amebocyte-agglutination agent solution was poured into 100 ml-centrifugal precipitation tubes. Into each of the tubes 50 ml of the blood of the horseshoe crab flowing out due to the inside pressure of the heart was added through the silicon tube, and the two liquids were gently mixed, followed immediately by 10 minutes' centrifugation at 3,000 rpm. The so formed layer of transparent, blue serum was discarded, and the amebocyte layer was washed well with freshly added anti-amebocyte-agglutination agent. The centrifugation and washing of the amebocyte were repeated, and all the amebocytes in the centrifugal tubes were collected into one of the tubes. The amebocyte was further washed with 60 ml of the isotonic solution containing no theophylline, subjected to the centrifugation, and washing which was discarded, and the same series of procedures were repeated once more. To the thus-obtained amebocyte which showed no agglutination, 30 ml of a pyrogen-free water was added per the amount of amebocyte obtained from 100 ml of the initially extracted horseshoe crab blood, stirred violently for an hour at room temperature, and the system was allowed to stand for a night in a cold place. Thereafter the amebocyte membranes were ruptured, and the contents were eluted into the water. The system was then separated into the precipitate of the membrane pieces and the transparent upper liquid layer by centrifuge, the latter being the object lysate.

All the tools, reagents, and solvent which came in contact with the amebocyte were first sterilized in an autoclave at 120°C. for 40 minutes, and then the pyrogen was removed by dry-heating at 170°C. for 2 hours. The tools were further silicon-coated in advance. The experiments were run in a clean room suited to prevent bacterial contamination for obvious reasons.

The thus-produced lysate could detect and determine endotoxin of $1 \times 10^{-3}$ µg/ml.

EXAMPLE 2

To an isotonic buffer solution obtained by adding a phosphate buffer solution having a pH of 6.8 to artificial sea water to a concentration of 0.01M, theobromine sodium acetate was dissolved to a concentration of 2mM, and the pH of the solution was readjusted to 6.8. 100 milliters of the so obtained anti-amebocyte-agglutination agent was sucked into a 200 ml-injection syringe mounted with a 13-gauge injection needle, and into which 100 ml of horseshoe crab's blood was extracted from the crab's heart by the puncturatio method similar to Example 1. The number of injection syringe was suitably increased according to the amount of blood extracted. The blood was gently mixed with the anti-amebocyte-agglutination agent in each syringe, and divided into 100-ml centrifugal tubes. Immediately thereafter the mixture was centrifugally separated for 10 minutes at 3,000 rpm, and the blue serum portion was discarded. The remaining amebocyte portion was washed well in the same anti-amebocyte-agglutination agent as first employed. The above centrifugation and washing were repeated, and the amebocyte was further washed in 60 ml of the isotonic buffer solution containing no theobromine sodium acetate, and separated from the washing by centrifuge. The washing and centrifugation were repeated twice, and thereafter 30 ml of a pyrogen-free aqueous solution containing 40 mM of NaCl, 20 mM of $MgSO_4$ and 4 mM of $CaCl_2$, per the amount of amebocyte obtained from 100 ml of the initially extracted horseshoe crab's blood, was added to the amebocyte showing no sign of agglutination. The system was stirred for an hour at room temperature, and allowed to stand in a cold place for a night. Whereupon the amebocyte content was eluted into the specified salt solution, which was subjected to centrifugation to provide a transparent lysate. The lysate was freeze-dried to be used as an endotoxin-detecting reagent, which could detect and determine as low as $1 \times 10^{-6}$ µg/ml of endotoxin.

EXAMPLE 3

The horseshoe crabs (*Limulus polyphemus*) serving as the experimental animals were disinfected with 70% ethanol at the back and thoracic-abdominal junction position. Into their hearts a 13-gauge injection needle connected with an approximately 20-cm long silicon tube was direcly inserted. Into an isotonic buffer solution prepared by dissolving sodium chloride in 0.01M tris buffer solution having a pH of 7.2 to a concentration of 2.95 wt %, theophylline was dissolved to a concentration of 2 mM, and the pH of the solution was readjusted to 7.2. Fifty ml each of the thus-prepared anti-amebocyte-agglutination agent was taken into 100-ml centrifugal precipitation tubes, and into which 50 ml each of the horseshoe crab's blood flowing out from the heart due to the inside pressure was added through the silicon tube. The blood was gently mixed with the anti-amebocyte-agglutination agent in each of the precipitation tubes, and immediately subjected to centrifugation for 10 minutes at 3,000 rmp. After discarding the transparent, blue serum portion, the same anti-ambebocyte-agglutination agent as used above was added to the remnant system, and the amebocyte portion was thoroughly washed therewith. The system was again subjected to the centrifugation and the wash forming the upper layer was discarded. The amebocyte was once more washed with the anti-amebocyte-agglutination agent, followed by the similar centrifugation. The amebocytes in the centrifugal tubes were collected into a single centrifugal tube, to which 60 ml of the isotonic buffer solution containing no theophylline was added. The series of washing and centrifugation procedures were repeated twice, and to the resulting amebocyte which showed no sign of agglutination, 30 ml of 20 mM $MgSO_4$ aqueous solution, per the amount of amebocyte obtained from 100 ml of the initially extracted horseshoe crab blood, was added. The system was violently stirred for an hour at room temperature, and allowed to stand in a cold place for a night. The amebocyte membranes were ruptured and the contents were eluted into the $MgSO_4$ aqueous solution. The sytem was centrifuged to separate the amebocyte's membrane pieces from the transparent upper liquid phase. The thus obtained lysate was freeze-dried and used as an endotoxin-detecting agent, which could detect and determine $5 \times 10^{-5}$ µg/ml of endotoxin.

EXAMPLE 4

To an isotonic buffer solution prepared by dissolving sodium chloride in a 0.01M tris buffer solution having a pH of 7.2 to a concentration of 2.95 wt %, caffeine was dissolved to a concentration of 2 mM, and its pH was readjusted to 7.2. Fifty ml each of the so-prepared anti-amebocyte-agglutination agent was taken into 100-ml centrifugal tubes, and into which again 50 ml each of horseshoe crab's blood was extracted through the silicon tube, by the cardiac puncturatio method similar to Example 1. The blood was gently mixed with the anti-amebocyte-agglutination agent in each of the centrifugal tubes, and immediately centrifuged for 10 minutes at 3,000 rpm. The so-formed transparent, blue serum portion was discarded, and the remaining amebocyte portion was washed well with freshly added anti-amebocyte-agglutination agent of identical composition as above. The centrifugal separation and subsequent washing were repeated twice. The amebocytes in the centrifugal tubes were collected into a single centrifugal tube. Then the amebocyte was washed with 60 ml of the isotonic buffer solution containing no caffeine, centrifugally separated from the washing, and the washing was discarded. This procedure was repeated twice, and to the so cleaned amebocyte which showed no sign of agglutination, 30 ml of 20 mM $MgSO_4$–4 mM $CaCl_2$ aqueous solution per the amount of amebocyte obtained from 100 ml of the initially extracted horseshoe crab blood was added. The system was violently stirred for an hour at room temperature, and allowed to stand in a cold place for a night. Whereupon the amebocyte membranes were ruptured, and the contents were eluted into the aqueous phase. The system was centrifugally separated into the precipitate of the amebocyte membrane pieces and the transparent upper liquid layer which was the object lysate.

The lysate was freeze-dried, and used as the endtoxin-detecting reagent, which could detect and determine as little as $5 \times 10^{-6}$ µg/ml of endotoxin.

EXAMPLE 5

An anti-amebocyte-agglutination agent was prepared by adding a phosphate buffer solution having a pH of 6.8 to artificial sea water to a concentration of 0.01M to form an isotonic buffer solution, dissolving therein theobromine sodium acetate to a concentration of 2 mM, and readjusting the pH of the solution to 6.8. One-hundred ml each of the agent was sucked into 200-ml injection syringes with 13-gauge needles, and into which 100 ml each of th horseshoe crabs' blood was extracted from their hearts by the puncturatio method similar to Example 1. The number of injection syringes was suitably increased according to the amount of the blood obtained. In each of the injection syringes the blood was gently mixed with the anti-amebocyte-agglutination agent, and the mixture was divided into 100-ml centrifugal precipitation tubes. Immediately the mixture was centrifuged for 10 minutes at 3,000 rpm, and the so-separated amebocyte portion was washed with the freshly added anti-amebocyte-agglutination agent same as that first prepared. The centrifugal separation and washing were repeated twice, and then the amebocyte was washed with 60 ml of the isotonic buffer solution containing no theobromine sodium acetate, and again followed by centrifugation. The washing and the centrifugation were also twice repeated.

Thirty ml of an aqueous solution containing 40 mM of NaCl and 4 mM of $CaCl_2$, per the amount of amebocyte obtained from 100 ml of the initially extracted horseshoe crab blood, was added to the thus-obtained amebocyte which showed no sign of agglutination, and the system was violently stirred for an hour at room temperature. Then the system was left standing in a cold place for a night, whereupon the amebocyte content was eluted into the aqueous phase. The transparent supernatant was separated from the precipitate of amebocyte membrane pieces by centrifuge, to provide the object lysate or pregel, which was freeze-dried and used as an endotoxin-detecting agent.

The lysate could detect and determine as low as $6.25 \times 10^{-5}$ µg/ml of endotoxin.

We claim:

1. In a process for the preparation of Limulina lysate comprising extracting the blood of horseshoe crabs (Limulina) into an isotonic buffer solution containing an agent which inhibits the agglutination of amebocyte, separating the amebocyte from said solution, breaking the amebocyte, and recovering Limulina lysate, the improvement comprising: (A) the addition of methyl derivatives of xanthine, or the acid addition or alkali salts thereof, having the formula

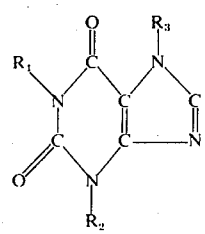

in which $R_1$, $R_2$, and $R_3$ each represent a hydrogen atom or a methyl group, at least one of $R_1$, $R_2$, and $R_3$ being a methyl group, as the agglutination-inhibiting agent of the amebocyte, the agglutination-inhibiting agent being present at a concentration of 0.5 to 2 mM in the mixture of the isotonic buffer solution and the blood; with an optional step of (B) further extracting the amebocyte content with 20 to 50 ml, per the amount of amebocyte obtained from 100 ml of the initially extracted blood, of an extraction solvent having a pH of 6.0 to 8.0 and containing at least one alkaline earth metal ion and, optionally, an alkali metal ion, with the provisos that the alkaline earth metal ions are present at a concentration of from 2 to 60 mM and the alkali metal ions are present at a concentration of from 10 to 150 mM, and a further optional step of (C) freeze-drying the so-obtained Limulina lysate containing extraction solution.

2. The process according to claim 1, in which the methyl derivatives of xanthine is theophylline, theobromine, or caffeine.

3. The process according to claim 1, in which the methyl derivatives of xanthine or the acid addition or alkali salts thereof are used at a concentration of 1 mM in the mixture of the isotonic buffer solution and blood obtained upon the blood extraction.

4. The process according to claim 1, in which the alkaline earth metal ion is magnesium.

5. The process according to claim 1, in which the extraction solvent contains alkaline earth metal ions and alkali metal ions.

6. The process according to claim 5, in which the extraction solvent is an aqueous solution containing 4 mM of calcium ion, 20 mM of magnesium ion, and 40 mM of sodium ion.

7. The process of claim 1 wherein 30 to 40 ml of the extraction solvent is added.

8. The process of claim 4 wherein the magnesium ion is present at a concentration of 5 to 50 mM.

9. The process of claim 8 wherein the magnesium ion is present at a concentration of 20 mM.

10. The process of claim 1 wherein the alkaline earth metal ion is calcium.

11. The process of claim 10 wherein the calcium ion is present at a concentration of 2 to 10 mM.

12. The process of claim 11 wherein the calcium ion is present at a concentration of 4 mM.

13. The process of claim 5 wherein the alkali metal ion is sodium ion present at a concentration of 40 mM.

14. The process of claim 5 wherein the extraction solvent is an aqueous solution containing 2 to 10 mM of calcium ion, 5 to 50 mM of magnesium ion, and 10 to 150 mM of sodium ion.

15. The extraction solution containing Limulina Lysate prepared according to the process of claim 14.

16. The extraction solution containing Limulina Lysate prepared according to the process of claim 6.

17. The process of claim 1 wherein optional step (C) is conducted.

18. The process of claim 1 in which optional step (B) is conducted and the extraction solvent contains an alkaline earth metal ion.

19. The freeze-dried powder derived from the Limulina Lysate extraction solution of claim 15.

* * * * *

UNITED STATES PATENT AND TRADEMARK OFFICE
CERTIFICATE OF CORRECTION

PATENT NO. : 3,954,663
DATED : May 4, 1976
INVENTOR(S) : Masaaki Yamamoto et al

It is certified that error appears in the above-identified patent and that said Letters Patent are hereby corrected as shown below:

Item 73, line 1, delete "Horinine", insert -- Hormone --

Signed and Sealed this

Third Day of August 1976

[SEAL]

Attest:

RUTH C. MASON
*Attesting Officer*

C. MARSHALL DANN
*Commissioner of Patents and Trademarks*